United States Patent [19]
Kamabuchi et al.

[11] Patent Number: 5,965,748
[45] Date of Patent: Oct. 12, 1999

[54] SUCCINIMIDE DERIVATIVE, PROCESS FOR PRODUCTION AND USE THEREOF

[75] Inventors: Akira Kamabuchi, Ibaraki; Naoki Takeyama, Settu; Jun Tomioka, Takarazuka; Haruyoshi Osaki, Toyonaka, all of Japan

[73] Assignee: Sumitomo Chemical Company, Limited, Osaka, Japan

[21] Appl. No.: 09/054,476

[22] Filed: Apr. 3, 1998

Related U.S. Application Data

[62] Division of application No. 08/738,283, Oct. 25, 1996, abandoned.

[30] Foreign Application Priority Data

Oct. 27, 1995 [JP] Japan ................................. 7-280233
Jun. 19, 1996 [JP] Japan ................................. 8-157783

[51] Int. Cl.⁶ ............................................................ C07D 207/46
[52] U.S. Cl. ................................................................. 548/542
[58] Field of Search ............................................... 548/542

[56] References Cited

FOREIGN PATENT DOCUMENTS 0632327   1/1995   European Pat. Off. .
9410608   5/1994   WIPO .

OTHER PUBLICATIONS

Patent Abstracts of Japan, vol. 950, No. 7 (JP 07–181678 A) Jul. 21, 1995.
Patent Abstracts of Japan, vol. 950, No. 9 (JP 07–244378 A) Sep. 19, 1995.

*Primary Examiner*—Robert W. Ramsuer
*Assistant Examiner*—Ebenezer Sackey
*Attorney, Agent, or Firm*—Birch, Stewart, Kolasch & Birch, LLP

[57] ABSTRACT

N-(10-camphorsulfonyloxy)-succinimide represented by the formula (I):

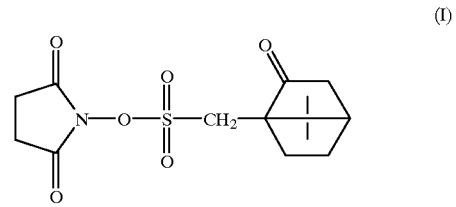

is provided, which can be produced by reacting N-hydroxysuccinimide with 10-camphorsulfonic acid, a salt thereof or a halide thereof. Using the compound as an acid generating agent, a resist composition can be obtained by including an alkali-soluble resin having a protective group removable by the action of an acid; and the resist composition is excellent in heat resistance, ratio of residual film thickness after developing, uniformity of film thickness, profile, photospeed and resolution and is improved in the time delay effect and attachment of pattern.

6 Claims, 2 Drawing Sheets

(a)

(b)

(a)

(b)

SUCCINIMIDE DERIVATIVE, PROCESS FOR PRODUCTION AND USE THEREOF

This application is a divisional of application Ser. No. 08/738,283, filed on Oct. 25, 1996, now abandoned, the entire contents of which are hereby incorporated by reference.

BACKGROUND OF THE INVENTION

1. Field of the Invention

The present invention relates to a novel succinimide derivative, a process for producing the same and an application of the same in the field of resist.

2. Background Information

In recent years, quarter-micron pattern formations have been demanded with the increase of the integration level of semi-conductive integral circuits. Particularly, the eximer laser lithography using krypton fluoride (KrF) or argon fluoride (ArF) as the light source has attracted attention because it enables production of 64 MDRAM and 256 MDRAM. Conventionally, near-ultraviolet rays have mainly been used in the lithography process. As the light source has been changed, however, the following properties have newly been required in addition to the conventionally required properties such as heat resistance, ratio of residual film thickness after developing (film retention ratio), profile and others a) high photospeed to KrF and ArF eximer laser light source, and b) high resolution.

Under these circumstances, has been proposed a type of resist, generally called chemical amplification type resist, which utilizes a chemical amplification effect of an acid-catalyst. In the chemical amplification type resist, the solubility of exposed part in an alkaline developing solution is realized by a reaction catalyzed by an acid which is generated from an acid generating agent by irradiation of radial rays and this affords a positive resist.

Conventionally, for the production of the chemical amplification type positive resist, polyvinylphenols in which the phenolic hydroxyls are protected by groups removable by the action of an acid have been used. The resist utilizing these resins has a defect that it is generally liable to be affected by its environment. Particularly, in the step of effecting the elimination reaction of the protective groups by heat treatment after exposure to rays (Post Exposure Bake; hereinafter, abbreviated as PEB), it is known that properties are greatly varied according to the period of standing before the heat treatment. This phenomenon is sometimes called Time Delay effect, and it may cause deterioration, of the resolution, T-top forming (T-shaping) in the pattern after development and bad repeatability of critical dimension.

It is considered that the reason for such a phenomenon is due to deactivation of the generated acid caused by basic substances such as ammonia and N-methylpyrrolidone which exist in an ambient atmosphere where the lithography is conducted and come into contact with the coating film. It is known, for example, that even if the content of ammonia in the air is as low as about 20 ppb, a pattern obtained by PEB carried out 30 minutes after exposure has a profile with remarkable T-shaping.

There is also a problem that, in the production of a quarter micron pattern, inferior etching caused by lying or peeling off of a smaller pattern is liable to occur.

An object of the present invention is to provide a novel compound which exerts excellent effects when used as an acid generating agent for a resist composition comprising an alkali-soluble resin having protective groups removable by the action of an acid.

Another object of the invention is to provide a resist composition, using such compound, which is excellent in photospeed and resolution and which is improved in the time delay effect and adhesion of pattern, while keeping heat resistance, ratio of residual film thickness after developing, uniformity of film thickness, profile and so on at high levels.

After extensive studies, the present inventors have successfully found a novel succinimide compound and discovered the fact that a resist composition comprising the compound together with an alkali-soluble resin having protective groups removable by the action of an acid is excellent in photospeed and resolution and improved in the time delay effect and adhesion of the pattern, while keeping heat resistance, ratio of residual film thickness after developing, uniformity of film thickness, profile and so on at high levels. Thus, the present invention has been completed.

SUMMARY OF THE INVENTION

The present invention provides N-(10-camphorsulfonyloxy)-succinimide represented by the formula (I):

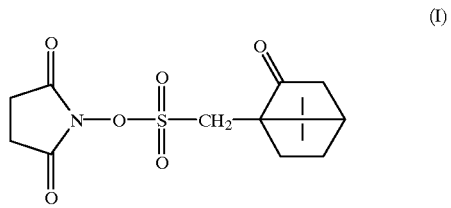

The present invention also provides a process for producing N-(10-camphorsulfonyloxy)succinimide of the formula (I) by reacting N-hydroxysuccinimide with 10-camphorsulfonic acid, a salt thereof or a halide thereof; an acid generating agent comprising, as an active ingredient, N-(10-camphorsulfonyloxy)-succinimide; and further, a resist composition comprising the acid generating agent described above together with an alkali-soluble resin having a protective group removable by the action of an acid.

DETAILED DESCRIPTION OF THE INVENTION

Figure 1:
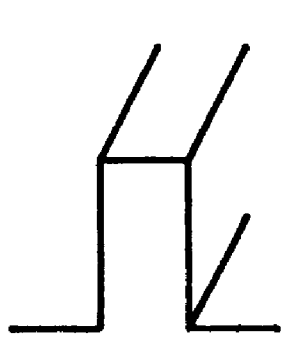
FIG. 1 shows a schematic perspective view of profiles in which (a) is the profile observed in Application Example 1 and (b) is the profile observed in Comparative Example 1.
Figure 1:
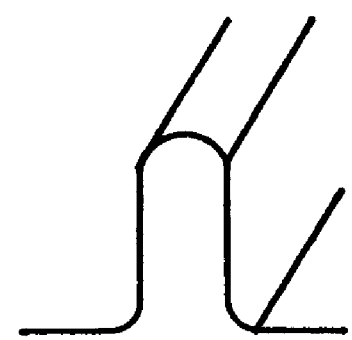
Figure 1A:
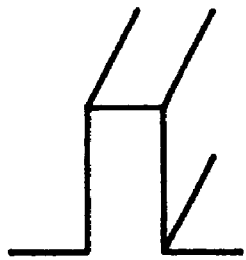
Figure 1B:
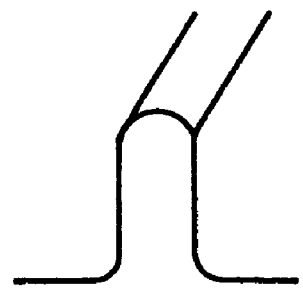

N-(10-camphorsulfonyloxy)succinimide represented by the formula (I) can be produced by a reaction of N-hydroxysuccinimide with 10-camaphorsulfonic acid, a salt thereof or a halide thereof. 10-Camphorsulfonic acid, the salt thereof or the halide thereof used here may either be in an optical active form or a racemic form. Among 10-camphorsulfonic acid, the salt thereof or the halide thereof, particularly preferred is a 10-camphorsulfonyl halide, which is preferably reacted with N-hydroxysuccinimide in the presence of a basic catalyst. Examples of halogen as the constituent of the 10-camphorsulfonyl halide include fluorine, chlorine, bromine and iodine.

It is preferred that, in this reaction, 10-camphorsulfonic acid, the salt thereof or the halide thereof is used in a molar ratio of 0.7–1.5, more preferably of 1.1–1.2, based on N-hydroxysuccinimide. If the molar ratio is less than 0.7, unreacted N-hydroxysuccinimide remains and if the ratio is more than 1.5, unreacted 10-camphorsulfonic acid or a derivative thereof remains, in a large amount in either cases, and purification after the reaction becomes difficult.

Examples of the basic catalyst used in the reaction of 10-camphorsulfonyl halide with N-hydroxysuccinimide include aliphatic amines such as triethylamine, cyclic amines such as pyridine, and inorganic bases such as sodium hydrogen carbonate, sodium carbonate or potassium carbonate. Among them, organic amines such as triethylamine and pyridine are preferred.

The reaction of N-hydroxysuccinimide with 10-camphorsulfonic acid, a salt thereof or a halide thereof is preferably carried out in a polar solvent. Examples of the polar solvent used here include one or more of hydrophilic solvents such as acetone, tetrahydrofuran, 1,4-dioxane, 1,3-dioxolane, dimethylformamide, acetonitrile, γ-butyrolactone and dimethylsulfoxide, one or more of hydrophobic solvents such as dichloromethane and chloroform, and water including ion exchanged water and distilled water. It is preferred that the polar solvent is used 2–10 times, more particularly 4–8 times, the total weight of the materials for reaction including N-hydroxysuccinimide and 10-camphorsulfonic acid, the salt thereof or the halide thereof. If the amount of the solvent is too large, the reaction takes a longer time and if the amount is too small, problems relating to the dissolution or the stirring torque may arise.

The reaction can usually be carried out at a temperature within a range of 20–50° C. When the temperature is too high, side reactions may increase and when the temperature is too low, the reaction takes a longer time. Usually, the reaction period is about 0.5–5 hours.

It is preferred to subject the reaction product containing N-(10-camphorsulfonyloxy) succinimide formed by a reaction of N-hydroxysuccinimide with 10-camphorsulfonyl halide to a treatment for removal of free acid, since free acid, particularly sulfonic acid such as 10-camphorsulfonic acid derived from 10-camphor-sulfonyl halide, the starting material, may give an unfavorable effect on the object of the present invention. By doing so, it is possible to produce N-(10-camphorsulfonyloxy)succinimide in which sulfonic acid is not remained and an acid generation agent effective in suppressing the delay effect and film-forming can be obtained more steadily.

After the reaction is terminated, salts of the basic catalyst formed by the reaction are removed as required and then the treatment for removing sulfonic acid is preferably conducted. The treatment for removing sulfonic acid may be any one insofar as it allows removal of sulfonic acid contaminating the reaction product and includes, for example, a method in which a solution containing the reaction product in a hydrophobic organic solvent is washed with an aqueous solution containing a neutral salt of an acid having an acidity weaker than that of sulfonic acid. For this purpose, when the reaction is carried out in a hydrophilic solvent, a hydrophobic organic solvent is added to the solution after the reaction or to the solution from which salts of the basic catalyst were removed. A preferred organic solvent is a solvent having a solubility in water of 9 g/100 g or less, and can appropriately dissolve 10-(camphorsulfonyloxy) succinimide. As used herein, the expression "a solvent having a solubility in water of 9 g/100 g or less" means that the maximum dissolving amount in 100 g of water at 20° C. is 9 g or less. Examples of such solvent include toluene, ethyl acetate, methylene chloride and n-heptane.

The acid having an acidity weaker than that of sulfonic acid includes, for example, acetic acid. The neutral salt used in the treatment for removing sulfonic acid includes, for example, sodium acetate, potassium acetate and ammonium acetate, among which sodium acetate is preferred. When the neutral salt of an acid having an acidity weaker than that of sulfonic acid is used, the amount of such a salt is 0.01 mole or more preferably 0.05–0.15 mole based on 10-camphorsulfonyl halide. Use of too much of the amount of the neutral salt is not preferred because metal salts or the like remain in N-(10-camphorsulfonyloxy)succinimide.

The treatment for removing sulfonic acid may accompany washing with a more dilute aqueous acid solution, for example, with aqueous acetic acid or oxalic acid solution having a concentration of about 0.1–1% by weight and further washing with water, after the washing with an aqueous solution of the neutral salt of an acid having an acidity weaker than that of a sulfonic acid as described above. This can minimize the content of a coexisting metal.

N-(10-camphorsulfonyloxy) succinimide produced by the reaction can be isolated after completion of the react on by suitable means for isolation. When the above mentioned treatment, i.e. removing sulfonic acid, is not conducted, it is preferred that the product is dissolved in a solvent having a solubility in water of 9 g/100 g or less, and the solution is shaken with water in order to minimize the metal content.

N-(10-camphorsulfonyloxy)succinimide formed by the reaction or treated as above can be crystallized from a suitable solvent. Examples of the solvent for crystallizing-out include halogenated hydrocarbons such as carbon tetrachloride or chloroform as such or as a main ingredient in a mixed solvent, or a mixed solvent of an aliphatic or alicyclic hydrocarbon such as n-heptane or cyclohexane and an aromatic hydrocarbon such as benzene, toluene or xylene. The temperature for crystallizing-out is preferably 40° C. or below and more particularly 25° C. or below.

N-(10-camphorsulfonyloxy) succinimide obtained in this way has an asymmetric carbon atom as shown by the formula (I) and may be in an optical active form or in racemic form. This compound is useful as an acid generating agent, particularly as an acid generating agent used in a resist composition comprising an alkali-soluble resin having protective groups removable by the action of an acid.

The alkali-soluble resin as a constituent of the resist composition of the present invention has protective groups removable by the action of an acid. Preferred base polymers in which the protective groups are introduced are those having an aryl group in which an hydroxy group or a carboxyl group is introduced. Specific examples of the base polymers include phenol novolak resins; cresol novolak resins; xylenol novolak resins; vinylphenol resins; isopropenylphenol resins; a copolymer of a vinylphenol or isopropenylphenol and a (meth)acrylic acid or a derivative thereof, acrylonitrile, styrene or a derivative thereof or the like; a copolymer of styrene or a derivative thereof and an acryl resin, methacryl resin, acrylic acid, metacrylic acid, maleic acid, maleic anhydride, acrylonitrile or the like; and a compound which contains silicon in the chain of the above described polymer.

The alkali-soluble resin in the resist composition according to the present invention may be a resin in which at least a part of the hydroxyl groups or the carboxyl groups in these base polymers is blocked by protective groups removable by the action of an acid. In other words, a resin in which at least a part of hydrogen atoms in the hydroxyl groups or carboxyl groups in these base polymers is substituted by such protective groups. Preferred protective group includes groups having the following chemical structures:

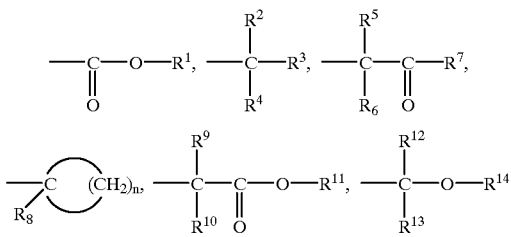

wherein n is an integer of 4–6;
$R^1$, $R^4$, $R^7$ and $R^{11}$ each independently represent linear alkyl, branched alkyl, cyclic alkyl, alkenyl, aryl or aralkyl;
$R^2$, $R^3$, $R^5$, $R^6$, $R^9$, $R^{10}$ and $R^{12}$ each independently represent hydrogen, linear alkyl, branched alkyl, cyclic alkyl, alkenyl, aryl or aralkyl;
$R^8$ is hydrogen, linear alkyl, branched alkyl, cyclic alkyl, alkenyl, aryl, aralkyl or alkoxy;
$R^{13}$ is hydrogen, linear alkyl, branched alkyl, cyclic alkyl, alkenyl, aryl or aralkyl; and
$R^{14}$ is linear alkyl, branched alkyl, cyclic alkyl, alkenyl, aryl or aralkyl; or
$R^{13}$ and $R^{14}$ together form unbranched alkylene of 3–6 carbon atoms.

Examples of the linear alkyl include those of 1–5 carbon atoms, examples of the branched alkyl include those of 3–8 carbon atoms and examples of the cyclic alkyl include those of 5–16 carbon atoms including cycloalkyl and cycloalkylalkyl. Examples of the alkenyl include those of 2–7 carbon atoms, examples of the aryl include those of 6–16 carbon atoms, typically phenyl or naphthyl, and examples of the aralkyl include those of 7–16 carbon atoms. Examples of the alkoxy include those of 1–5 carbon atoms. These groups may have substituents. Examples of substituents which may exist on the linear alkyl, branched alkyl or alkenyl include halogen. Examples of substituents which may exist on the cycloalkane ring as the cyclic alkyl include halogen and examples of substituents on the aromatic ring such as benzene ring or naphthalene ring as the aryl or aralkyl include halogen and nitro. Any hydrocarbon group such as alkyl or the like may be substituted on said cycloalkane ring or aromatic ring within the above range of number of carbon atoms.

The resist composition according to the present invention comprises the alkali-soluble resin and the acid generating agent and, if necessary, may further comprise additives conventionally used in this field such as an electron donor, dissolution inhibitor, photo-sensitizer, dye, adhesion promoter and the like. It is preferred that the resist composition contains the alkali-soluble resin in a range of 20–90% by weight and the acid generating agent in a range of 0.1–20% by weight based on the total weight of solid components.

The resist composition of the present invention is usually prepared by mixing the above described components into a solvent such that concentration of the total solid components is 10–50% by weight. It is applied on a substrate such as a silicone wafer. The solvent used here may be any one insofar as it dissolves all the components and can be any one conventionally used in this field. Examples include glycol ether esters such as ethyl cellosolve acetate, methyl cellosolve acetate, propylene glycol monomethyl ether acetate and propylene glycol monoethyl ether acetate; glycol mono- or di-ethers such as ethyl cellosolve, methyl cellosolve, propylene glycol monomethyl ether, propylene glycol monoethyl ether and diethylene glycol dimethyl ether; esters such as ethyl lactate, butyl acetate and ethyl pyruvate; cyclic esters such as γ-butyrolactone; ketones such as 2-heptanone, cyclohexanone and methyl isobutyl ketone; and aromatic hydrocarbons such as xylene. These solvents may be used independently or as a mixture of two or more.

N-(10-camphorsulfonyloxy)succinimide obtained in the present invention is useful as an acid generating agent for a resist composition and particularly as an acid generating agent for a resist composition comprising an alkali-soluble resin having protective groups removable by the action of an acid. The resist composition, using such compound as an acid generating agent is excellent in photospeed and resolution and is improved in the time delay effect and adhesion property, while keeping heat resistance, ratio of residual film thickness after developing, uniformity of film thickness, profile and so on at high levels.

EXAMPLES

The present invention will further be illustrated in more detail by means of Examples, which, however, should not be construed as limitation upon the scope of the invention. In Examples, % and parts for describing content and amount are weight based unless otherwise specified.

Example 1

Into a 200 ml four-necked flask were charged 7.41 g of N-hydroxysuccinimide, 18.13 g of (±)-10-camphorsulfonyl chloride and 127.69 g of acetonitrile and, after stirring at 25° C. for 30 minutes, 7.89 g of triethylamine was added thereto over 20 minutes. The mixture was filtered after stirring for an additional 3 hours, and the filter cake was washed with 36.63 g of acetonitrile. To the combined filtrate and washing was added 367.88 g of ethyl acetate and the mixture was washed three times with 180.66 g of distilled water and concentrated. To the concentrate was added 11.97 g of acetone and the mixture was refluxed while 119.66 g of carbon tetrachloride was added. Crystals formed upon cooling were filtered and 27.37 g of wet cake thus obtained was dried with warm air at 40° C. for twenty-four hours to give 19.41 g of N-(10-camphor-sulfonyloxy)succinimide.

MS: SIMS(FAB), 330 $(M+H)^+$ $^1$H-NMR (dimethyl sulfoxide), (ppm): 0.83 (s, 3H); 1.02 (s, 3H); 1.41–1.50 (m, 1H); 1.60–1.70 (m, 1H); 1.93–2.03 (m, 2H); 2.09–2.13 (m, 1H); 2.16–2.26 (m, 1H); 2.34–2.44 (m, 3H); 2.80 (s, 4H); 3.79–3.96 (m, 2H). $^{13}$C-NMR (dimethyl sulfoxide), (ppm): 19.01, 25.14, 25.38, 26.14, 41.76, 42.28, 47.96, 51.32, 57.88, 170.30, 212.84.

Example 2

Into a 200 ml four-necked flask were charged 17.26 g of N-hydroxysuccinimide, 34.90 g of (+)-10-camphorsulfonyl chloride and 260.81 g of 1,4-dioxane and, after stirring at 25° C. for 30 minutes, 15.03 g of triethylamine was added thereto over 30 minutes. After stirring for an additional 4 hours, 661.21 g of toluene was added to the reaction mass and the mass was washed with 335.61 g of 0.5% aqueous oxalic acid solution. Phases were separated and the organic layer was washed 6 times with 335.61 g of distilled water and concentrated. To the concentrate was added 23.39 g of ethyl acetate and the mixture was heated to 60° C. Then a mixture of 79.53 g of n-heptane and 154.37 g of toluene was added and cooled to 25° C. or below. Crystals formed were filtered and the obtained wet cake was dried with warm air at 40° C. for twenty-four hours to give 34.52 g of N-(10-camphorsulfonyloxy)succinimide.

Example 3

Into 66 parts of propylene glycol monomethyl ether acetate were dissolved 13.5 parts of a polymer which was obtained by a method described in JP-A-5-181279 and in which 20% by mole of hydroxyl groups in poly(p-vinylphenol) was converted to tert-butoxycarbonylmethyl ether, 1.2 part of N-(10-camphorsulfonyl-oxy)succinimide obtained in Example 1, 0.405 part of 2-hydroxycarbazole (manufactured by Aldrich) as an electron donor and 66 parts of propyleneglycolmonomethyl ether acetate, and the mixture was passed through a fluorine resin filter having a pore size of 0.2 μm to give resist solution A.

Resist solution A obtained above was applied with a spin coater onto a silicone wafer washed according to the conventional method such that a film having a thickness after drying of 0.7 μm is formed. Then the silicone wafer was pre-baked on a hot plate at100° C. for 1 minute. The film after pre-baking was irradiated with a KrF eximer laser stepper [-"NSR-1755 EX8A", manufactured by Nikon NA=0.45] having an exposure wave length of 248 nm through a chromium mask having a pattern. The exposed wafer was subjected to post-baking (PEB) on a hot plate at 95° C. for 90 seconds. Then the wafer was developed with 2.38% aqueous tetramethyl ammonium hydroxide to give a positive pattern- The obtained positive pattern was assessed by the following methods and the results are shown in Table 1.

Photospeed: A 0.3 μm line-and-space cross section was observed with a scanning electron microscope and the photospeed (optimized dose) was obtained from a light exposure which gave a line-and-space of 1:1 at the best focus.

Resolution: A minimum width of line-and-space splitting without loss of the film thickness by a light exposure at the optimized dose was taken as the resolution.

Profile: A 0.3 μm line-and-space cross section at a light exposure at the optimized dose was observed with a scanning electron microscope.

Lying of smaller pattern: Lying of the resist was observed and assessed using a 3 grades scoring system in which ○ means no lying, Δ partly lying, and X most lying.

The assessment was also conducted for all the test subjects on wafers which were baked after 1 hour standing from exposure.

Comparative Example 1

The procedure in Application Example 1 was substantially repeated except that 0.405 part of a compound (manufactured by Midori Kagaku) represented by the following formula:

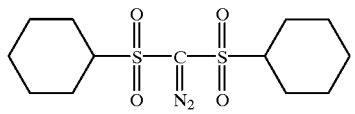

was used in place of N-(10-camphorsulfonyl-oxy)succinimide used in Application Example 1 to give resist solution B. The resist solution B was assessed in the same manner as in Application Example 1 and the results are included in Table 1.

TABLE 1

| | Photospeed | Resolution | Profile* | Lying of pattern |
|---|---|---|---|---|
| Application Example 1 | | | | |
| PEB immediately after exposure | 28 mJ/cm² | 0.29 μm | (a) | ○ |
| PEB 1 hour after exposure | 32 mJ/cm² | 0.30 μm | (a) | ○ |
| Comparative Example 1 | | | | |
| PEB immediately after exposure | 122 mJ/cm² | 0.35 μm | (b) | Δ |
| PEB 1 hour after exposure | Not resolved | Not resolved | Not resolved | Not resolved |

*(a) and (b) in Profile mean that shapes were (a) and (b), respectively, in the FIG. 1.

Example 4

(1) Production of N-(10-camphorsulfonyloxy)succinimide

Into a 2 liter four-necked flask were charged 46.23 g of N-hydroxysuccinimide, 93.45 g of (+)-10-camphorsulfonyl chloride and 698.39 g of acetone. Thereto, after stirring at 25° C. for 30 minutes, 38.41 g of triethylamine was added over 30 minutes. The mixture was filtered after stirring of an additional 3 hours, and the filtrate was washed with 186.90 g of acetone. To the combined filtrate and washing was added 177.06 g of ethyl acetate and 708.23 g of toluene. The mixture was washed with a solution containing 3.06 g of sodium acetate in 559.06 g of distilled water and the organic layer was washed further with 588.71 g of distilled water. Then the organic layer was washed with 588.71 g of 0.5% aqueous oxalic acid solution and further washed four times each with 588.71 g of water. The organic layer was concentrated to give 133.72 g of an oily substance, to which 334.30 g of toluene was added. The mixture was heated to 50° C. to form a uniform solution. To the solution was added dropwise a mixed solvent of 133.72 g of toluene and 200.58 g of n-heptane with stirring. After the addition, the solution was cooled to 25° C. over 3 hours and stirred for 1.5 hour after cooling to 5° C. Precipitates formed were filtered and dried overnight at 45° C. to obtain 102.40 g of N-(10-camphorsulfonyloxy)succinimide.

(2) Preparation and Assessment of Resist

Into a mixture of 52 parts of propylene glycol monomethyl ether acetate and 13 parts of ethyl lactate were dissolved 13.5 parts of a polymer which was obtained by a method described in JP-A-5-181279 and in which 30% by mole of hydroxyl groups in poly(p-vinylphenol) was converted to tert-butoxycarbonylmethyl ether, 1.0 part of N-(10-camphorsulfonyl-oxy)succinimide obtained in above (1), 0.27 part of 2-hydroxycarbazole as an electron donor and 0.08 part of N-methyl-2-pyrrolidone as a basic compound. The mixture thus obtained was passed through a fluorine resin filter having a pore size of 0.2 μm to give a resist solution.

The resist solution obtained above was coated with a spin coater onto a silicone wafer washed according to the conventional method such that a film having a thickness after crying of 0.7 μm is formed. Then the silicone wafer was pre-baked on a hot plate at 100° C. for 90 seconds. The film after pre-baking was irradiated with a KrF eximer laser stepper ["NSR-1755 EX8A", manufactured by Nikon Ltd.] having an exposure wave length of 248 nm through a chromium mask having a pattern. The exposed wafer was subjected to post-baking (PEB) on a hot plate at 100° C. for 90 seconds. Then the wafer was developed with 2.38% aqueous tetramethyl ammonium hydroxide to give a positive pattern. The obtained positive pattern was assessed by the methods as described in Application Example 1. Photospeed is 71 mJ/cm² when PEB is conducted either immediately after the exposure or 15 minutes after the exposure. Resolution is 0.27 μm when PEB is conducted either immediately after the exposure or 15 minutes after the exposure. Profile as good as that obtained in Application Example 1 was obtained when PEB is conducted either immediately after the exposure or 15 minutes after the exposure.

What is claimed is:

1. A process for producing N-(10-camphorsulfonyloxy)-succinimide represented by the formula (I):

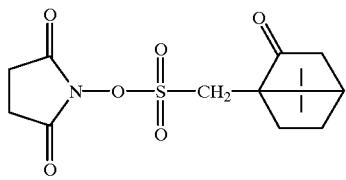

(I)

which comprises reacting N-hydroxysuccinimide with 10-camphorsulfonic acid, a salt thereof or a halide thereof.

2. The process according to claim 1, in which the 10-camphorsulfonyl halide is used and the reaction is carried out in the presence of a basic catalyst.

3. The process according to claim 1 or 2, in which the reaction is carried out in a polar solvent.

4. A process according to claim 1 wherein the reaction product is subjected to a treatment for removal of sulfonic acid.

5. The process according to claim 4, in which the treatment for removal of sulfonic acid comprises a step of washing a solution containing the reaction product in a hydrophobic organic solvent with an aqueous solution containing a neutral salt of an acid having an acidity weaker than that of sulfonic acid.

6. The process according to claims 1 or 4, in which the product is crystallized out from a halogenated hydrocarbon solvent, or a mixed solvent of an aliphatic or alicyclic hydrocarbon and an aromatic hydrocarbon.

* * * * *